United States Patent
Hirschmann et al.

(10) Patent No.: US 6,514,579 B1
(45) Date of Patent: Feb. 4, 2003

(54) TN AND STN LIQUID CRYSTAL DISPLAYS

(75) Inventors: Harald Hirschmann, Darmstadt (DE); Georg Weber, Erzhausen (DE)

(73) Assignee: Merck Patent Gesellschaft, Darmstadt (DE)

(*) Notice: Subject to any disclaimer, the term of this patent is extended or adjusted under 35 U.S.C. 154(b) by 49 days.

(21) Appl. No.: 09/608,155

(22) Filed: Jun. 30, 2000

(30) Foreign Application Priority Data

Jun. 30, 1999 (DE) .......................... 199 30 211

(51) Int. Cl.$^7$ .................. C09K 19/30; C09K 19/20; C09K 19/34; C09K 19/12
(52) U.S. Cl. .............. 428/1.1; 252/299.61; 252/299.63; 252/299.66; 252/299.67
(58) Field of Search ................. 252/299.66, 299.63, 252/299.01, 299.61, 299.67; 428/1.1

(56) References Cited

U.S. PATENT DOCUMENTS 6,017,469 A * 1/2000 Reiffenrath et al. .... 252/299.63
6,080,451 A * 6/2000 Hirschmann et al. ........ 428/1.1

FOREIGN PATENT DOCUMENTS

DE 19844321 * 4/1999

* cited by examiner

Primary Examiner—Shean C. WU
(74) Attorney, Agent, or Firm—Millen, White, Zelano & Branigan, P.C.

(57) ABSTRACT

The invention relates to TN and STN displays having very short switching times and good steepness and angular dependence and to the novel nematic liquid crystal mixtures employed therein, which are distinguished by comprising at least one compound of formula IA,

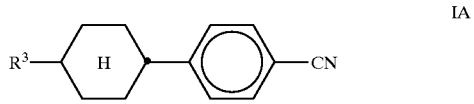

IA where $R^3$ is an alkenyl group having from 2 to 7 C atoms, and comprising at least one compound of formula IB,

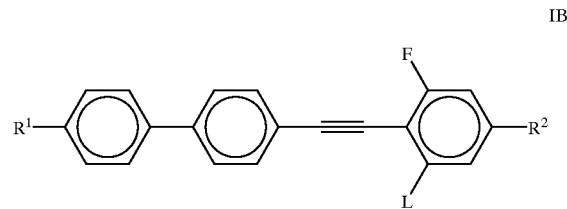

IB where $R^1$ and $R^2$ each, independently of one another, are an alkyl, alkoxy or alkenyl group having from 1 to 12 C atoms, with the additional option of 1 or 2 non-adjacent $CH_2$ groups being replaced by —O—, —CH=CH—, —CO—, —OCO— or —COO— in such a way that O atoms are not linked directly to one another, and L is H or F.

13 Claims, No Drawings

TN AND STN LIQUID CRYSTAL DISPLAYS

The invention relates to twisted nematic (acronym TN) and supertwisted nematic (acronym STN) liquid crystal displays having very short switching times and good steepness and angular dependence and to the novel nematic liquid crystal mixtures employed therein.

TN displays are known, e.g. from M. Schadt and W. Helfrich, Appl. Phys. Lett., 18, 127 (1971). STN displays are known, e.g. from EP 0 131 216 B1; DE 34 23 993 A1; EP 0 098 070 A2; M. Schadt and F. Leenhouts, 17th Freiburg Conference on Liquid Crystals (8–10/04/87); K. Kawasaki et al., SID 87 Digest 391 (20.6); M. Schadt and F. Leenhouts, SID 87 Digest 372 (20.1); K. Katoh et al., Japanese Journal of Applied Physics, Vol. 26, No. 11, L 1784–L 1786 (1987); F. Leenhouts et al., Appl. Phys. Lett. 50 (21), 1468 (1987); H. A. van Sprang and H. G. Koopman, J. Appl. Phys. 62 (5), 1734 (1987); T. J. Scheffer and J. Nehring, Appl. Phys. Lett. 45 (10), 1021 (1984), M. Schadt and F. Leenhouts, Appl. Phys. Lett. 50 (5), 236 (1987), and E. P. Raynes, Mol. Cryst. Liq. Cryst. Letters Vol. 4 (1), pp. 1–8 (1986). The term STN herein comprises any relatively strongly twisted display element having a twist angle amounting to between 160° and 360°, for example the display elements according to Waters et al. (C. M. Waters et al., Proc. Soc. Inf. Disp. (New York) (1985) (3rd Intern. Display Conference, Kobe, Japan), the STN LCDs (DE-A-35 03 259), SBE LCDs (T. J. Scheffer and J. Nehring, Appl. Phys. Lett. 45 (1984) 1021), OMI LCDs (M. Schadt and F. Leenhouts, Appl. Phys. Lett. 50 (1987), 236, DST LCDs (EP-A 0 246 842) or BW STN LCDs (K. Kawasaki et al., SID 87 Digest 391 (20.6)).

STN displays in particular are distinguished, compared with standard TN displays, by considerably better slopes of the electro-optical characteristic curve and the attendant better contrast values and by a significantly reduced angular dependence of the contrast. Of particular interest are TN and STN displays having a very short switching time, especially at lower temperatures. To achieve short switching times it has hitherto been the practice to optimize the rotational viscosities of the liquid crystal mixtures, by employing usually monotropic additives having a relatively high vapour pressure. The switching times achieved were not, however, adequate for all applications.

To achieve a steep electro-optical characteristic curve in TN and STN displays, the liquid crystal mixtures should have relatively large values of $K_3/K_1$ and relatively small values of $\Delta\epsilon/\epsilon_1$.

Beyond optimized contrast and optimized switching times, such mixtures are subject to further important requirements:

1. wide d/p window
2. high chemical long-term stability
3. high electrical resistance
4. low frequency dependence and temperature dependence of the threshold voltage.

The parameter combinations achieved are still inadequate by a long shot, especially for high-multiplex, but also for low- and medium-multiplex STNs (1/400). One reason for this is that the effects of material parameters on the various requirements pull in opposite directions.

There is therefore still a great need for TN and STN displays, especially for high-resolution displays (XGA), having very short switching times in conjunction with a wide operating temperature range, a steep characteristic curve, good angular dependence of contrast and low threshold voltage, which comply with the above-specified requirements.

It is an object of the invention to provide TN and STN displays which do not have the above-specified draw-backs or which have them only to a lesser extent and at the same time have low threshold voltages and very good steepness.

Upon further study of the specification and appended claims, further objects and advantages of this invention will become apparent to those skilled in the art.

We have now found that this object can be achieved if nematic liquid crystal mixtures are employed which comprise compounds of formula IA

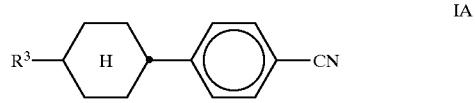

IA in conjunction with alkynyl-bonded compounds of formula IB,

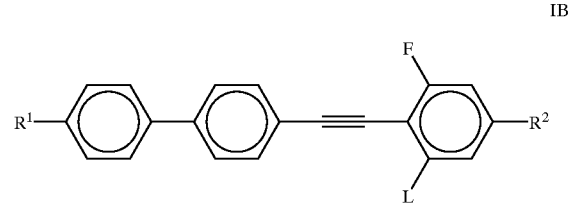

IB where
  $R^1$ and $R^2$ each, independently of one another, are an alkyl, alkoxy or alkenyl group having from 1 to 12 C atoms, with the additional option of 1 or 2 non-adjacent $CH_2$ groups being replaced by —O—, —CH=CH—, —CO—, —OCO— or —COO— in such a way that O atoms are not linked directly to one another,
  $R^3$ is an alkenyl group having from 2 to 7 C atoms, and
  L is H or F.

The use of the compounds of formulae IA and IB in the mixtures for TN and STN displays according to the invention results in
  low viscosities,
  wide nematic phase ranges,
  a steeply sloping electro-optical characteristic curve, and
  low threshold voltages.

The compounds of formulae IA and IB, in particular, cause a distinct increase in the steepness of TN and STN mixtures whilst at the same time reducing the threshold voltage.

The mixtures according to the invention are further distinguished by the following advantages:
  they exhibit low temperature dependence of the threshold voltage and the operating voltage,
  they have short switching times even at low temperatures,
  they result in long persistence times in the display at low temperatures.

The invention therefore relates to a liquid crystal display comprising
  two substrates which, together with an edging, form a cell,
  contained in the cell, a nematic liquid crystal mixture having positive dielectric anisotropy,
  electrode layers having alignment layers on the insides of the substrates,
  a pre-tilt angle between the longitudinal axis of the molecules at the surface of the substrates and the substrates of from 0 degrees to 30 degrees, and a twist angle of the liquid crystal mixture in the cell which, from alignment layer to alignment layer, amounts to between 22.5° and 600°, a nematic liquid crystal mixture comprising
a) 20–90 wt % of a liquid-crystalline component A, consisting of one or more compounds having a dielectric anisotropy of more than +1.5;
b) 10–80 wt % of a liquid-crystalline component B, consisting of one or more compounds having a dielectric anisotropy of between −1.5 and +1.5;
c) 0–20 wt % of a liquid-crystalline component C, consisting of one or more compounds having a dielectric anisotropy of less than −1.5 and
d) optionally an optically active component D in such an amount that the ratio between layer thickness (spacing of the substrates) and natural pitch of the chiral nematic liquid crystal mixture is from about 0.2 to 1.3, characterized in that component A of the mixture comprises at least one compound of formula IA,

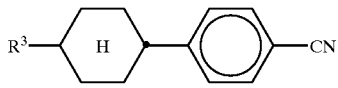

IA where
$R^3$ is an alkenyl group having from 2 to 7 C atoms, and the mixture comprises at least one compound of formula IB,

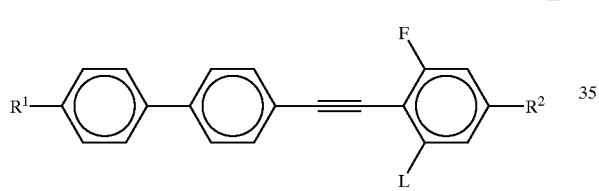

IB where
$R^1$ and $R^2$ each, independently of one another, are an alkyl, alkoxy or alkenyl group having from 1 to 12 C atoms, with the additional option of 1 or 2 non-adjacent $CH_2$ groups being replaced by —O—, —CH=CH—, —CO—, —OCO— or —COO— in such a way that O atoms are not linked directly to one another, and
L is H or F.

The invention also relates to corresponding liquid crystal mixtures for use in TN and STN displays, especially in medium- and low-multiplexed STN displays.

Particularly preferred compounds of formula IA are those of the following formulae

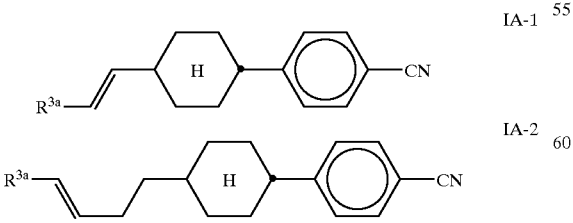

IA-1

IA-2 where $R^{3a}$ is H, $CH_3$, $C_2H_5$ or n-$C_3H_7$.

Particularly preferred compounds of formula IB are those where L is F.

The component A, in addition to the compounds of formula IA, preferably further comprises one or more compounds of formulae II and/or III,

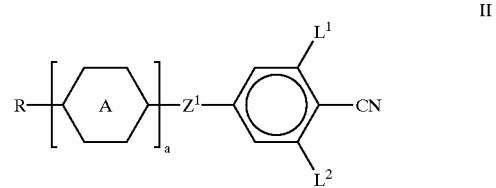

II

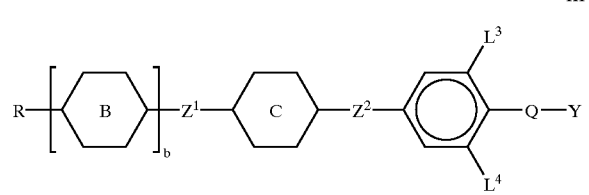

III where
R is an alkyl, alkoxy or alkenyl group having from 1 to 12 C atoms, with the additional option of 1 or 2 non-adjacent $CH_2$ groups being replaced by —O—, —CH=CH—, —CO—, —OCO— or —COO— in such a way that O atoms are not linked directly to one another,

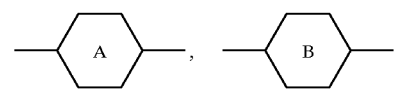

and

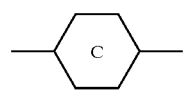

each, independently of one another, are

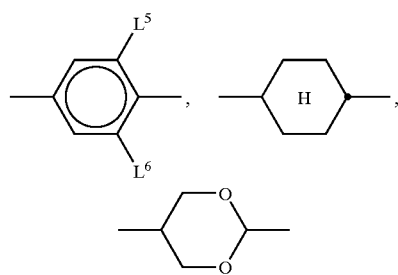

or

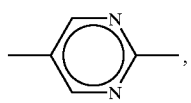

$L^1$ to $L^6$ each, independently of one another, are H or F,
$Z^1$ is —COO—, —$CH_2CH_2$— or a single bond,
$Z^2$ is —$CH_2CH_2$—, —COO—, —C≡C— or a single bond, Q is —CF$_2$—, —CHF—, —OCF$_2$—, —OCHF— or a single bond,
Y is F or Cl,
a is 1 or 2, and
b is 0 or 1,
where, regarding formula II, the compounds of formula IA as specified above are excluded.

Preferred compounds of formula II correspond to the subformulae IIa to IIh:

IIa
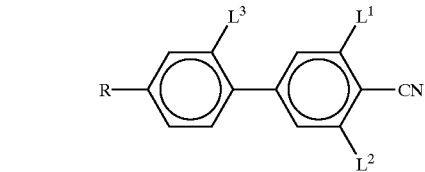

IIb
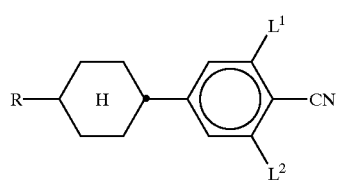

IIc
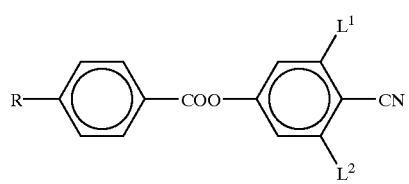

IId
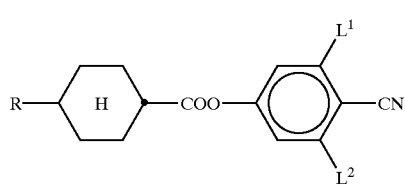

IIe
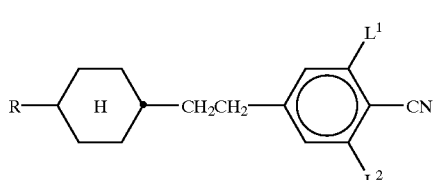

IIf
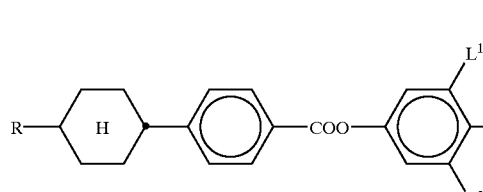

IIg
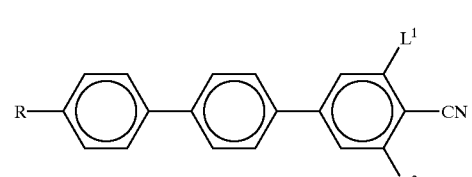

IIh
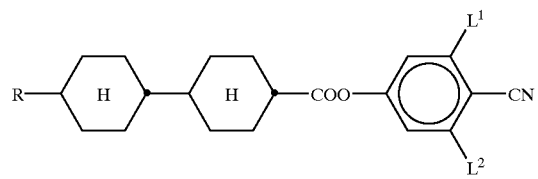

where R, L$^1$, L$^2$ and L$^3$ have the above-specified meanings and, in the case of compounds of formula IIb where L$^1$ and L$^2$ are H, R is an alkyl or alkoxy group.

Particularly preferred are mixtures comprising one or more compounds of the following subformulae IIb1
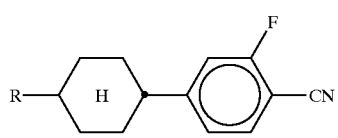

IIb2
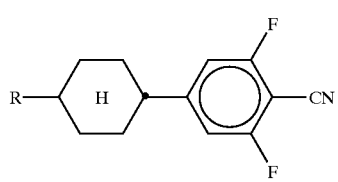

IIc1
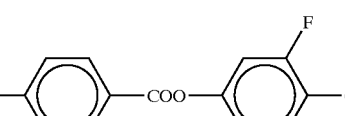

IIc2
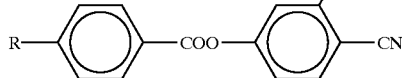

IIf1
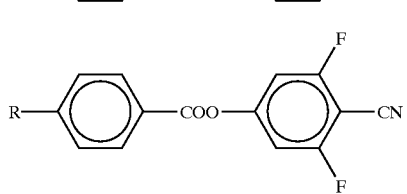

IIf2
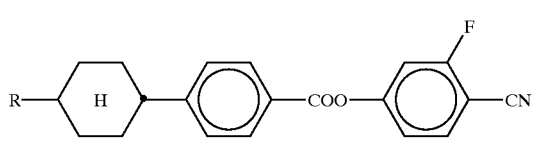

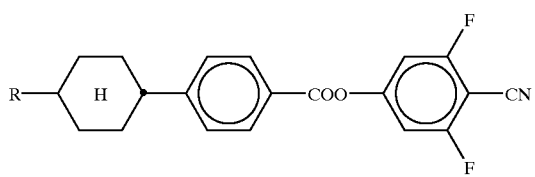

where R has the above-specified meaning.

Also preferred are mixtures comprising one or more compounds of formula IIh, where L$^2$ is H and L$^1$ is H or F, especially F.

In a particularly preferred embodiment, component A additionally comprises compounds of formulae AI to AIV:

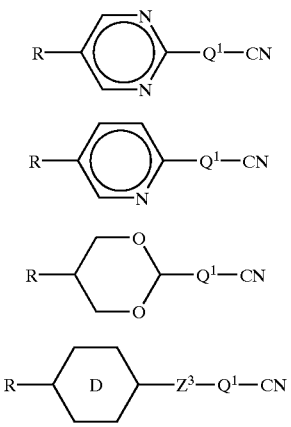

where
- R is an alkyl, alkoxy or alkenyl group having from 1 to 12 C atoms, with the additional option of 1 or 2 non-adjacent CH$_2$ groups being replaced by —O—, —CH=CH—, —CO—, —OCO— or —COO— in such a way that O atoms are not linked directly to one another,

and Q$^1$ each, independently of one another, are

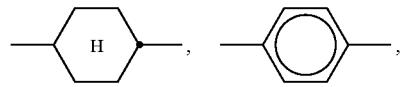

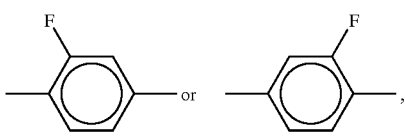

Z$^3$ is

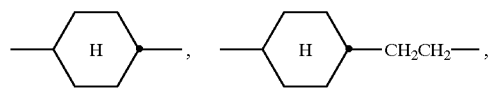

—CH$_2$CH$_2$—, —CO—O—, —O—CO— or a single bond.

Preferably, the mixtures according to the invention comprise one or more polar compounds having a high clearing point, selected from the group consisting of the compounds AIV1 to AIV4:

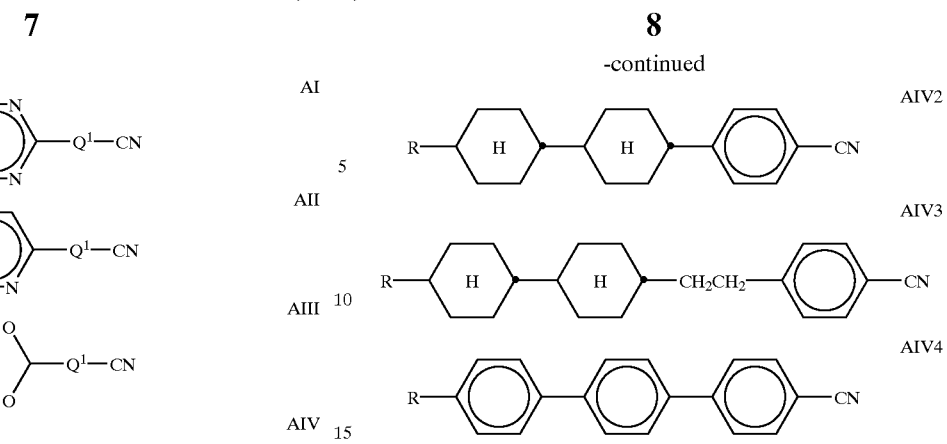

In the compounds AIV1 to AIV4, the 1,4-phenylene rings can also be substituted laterally by one or two fluorine atoms. Preferred compounds of this type are the compounds of formulae AIV1-1, AIV1-2 and AIV1-3:

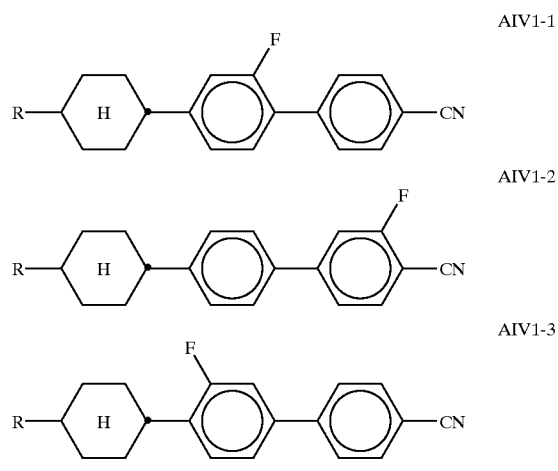

In the mixtures according to the invention which comprise compounds of formulae AIV1 to AIV4, the proportion of these compounds is preferably from about 2 to 25%.

Preferred compounds of formula III correspond to the subformulae IIIa–IIIv:

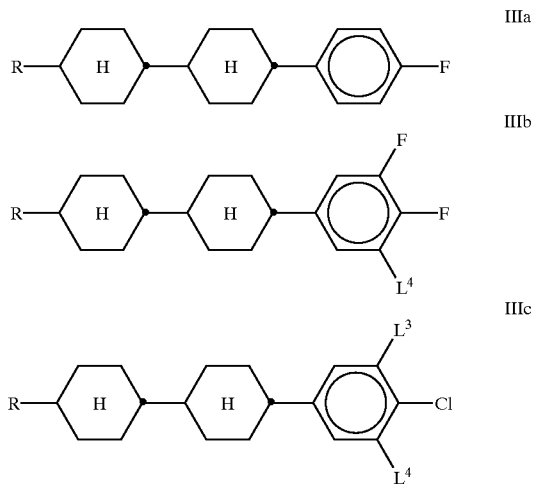

-continued

IIId, IIIe, IIIf, IIIg, IIIh, IIIi, IIIj, IIIk, IIIm, IIIn, IIIo, IIIp, IIIq, IIIr, IIIs, IIIt, IIIu

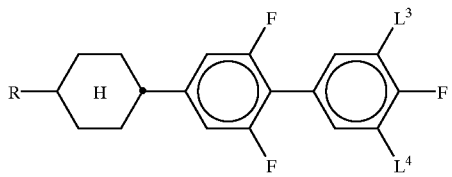
IIIv where R has the above-specified meaning and $L^3$ and $L^4$, independently of one another, are H or F.

Particularly preferred among the compounds of formulae IIIa to IIIv are those where $L^4$ is F, also those where $L^3$ and $L^4$ are F.

Preferred mixtures comprise not only one or more compounds of formulae IA and IB, but also one, two, three or more compounds of formulae IIa, IIb, IIc, IIf, IIIb, IIId, IIIf, IIIh, IIIi, IIIm, IIIs, IIIt or IIIu, preferably one or more compounds of formula IIIb, IIId, IIIh, IIIt or IIIu and from one to four compounds of formulae IA and IB and from one to three compounds of formulae IIa, IIb and/or IIc.

In the preferred compounds mentioned hereinabove and hereinafter of the subformulae relating to formulae II and III, R preferably is, unless noted otherwise, straight-chain alkyl, alkenyl or alkoxy, in particular alkyl, having from 1 to 12 C atoms, in particular having from 1 to 7 C atoms.

Also preferred are mixtures comprising one or more compounds of subformula IIIb1

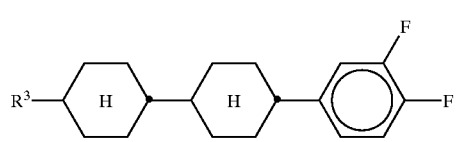
IIIb1 where $R^3$ has the meaning specified in formula Ib.

$R^3$ in the compounds of formula IIIb1 is particularly preferably vinyl, 1E-propenyl, 1E-butenyl, 3E-butenyl, 3E-pentenyl, particularly vinyl.

The individual compounds, e.g. of formulae II and III and their subformulae, or alternatively other compounds which can be used in the STN displays according to the invention, are either known or they can be prepared in a manner similar to that for the known compounds.

Preferred liquid crystal mixtures comprise one or more compounds of component A, preferably in a proportion of from 15% to 75%, particularly preferably from 20% to 65%. These compounds have a dielectric anisotropy $\Delta\varepsilon \geq +3$, in particular $\Delta\varepsilon \geq +8$, particularly preferably $\Delta\varepsilon \geq +12$.

Preferred liquid crystal mixtures comprise one or more compounds of component B, preferably from 10 to 65%. The compounds of group B are distinguished, in particular, by their low values of rotational viscosity $\gamma_1$.

Component B preferably comprises one or more compounds selected from the group consisting of the compounds of formulae IV1 to IV9:

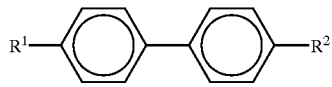
IV1

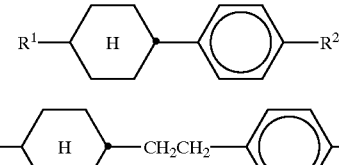
IV2

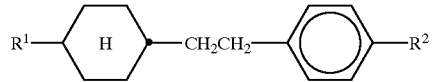
IV3

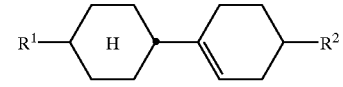
IV4

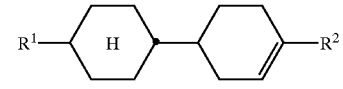
IV5

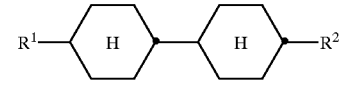
IV6

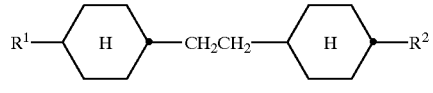
IV7

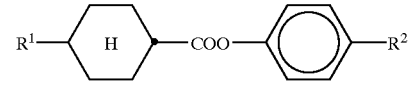
IV8

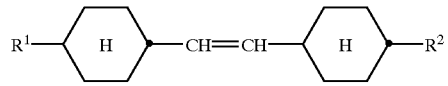
IV9 where $R^1$ and $R^2$ have the meaning specified in formula IB.

Component B additionally comprises one or more compounds selected from the group consisting of the compounds of formulae IV10 to IV24,

IV10

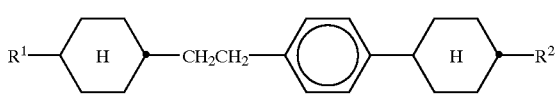
IV11

IV12

IV13

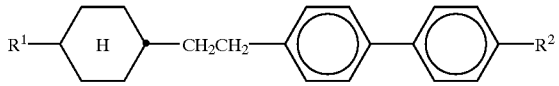
IV14

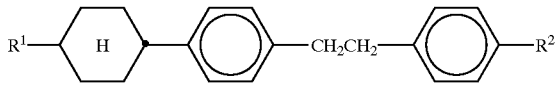
IV15

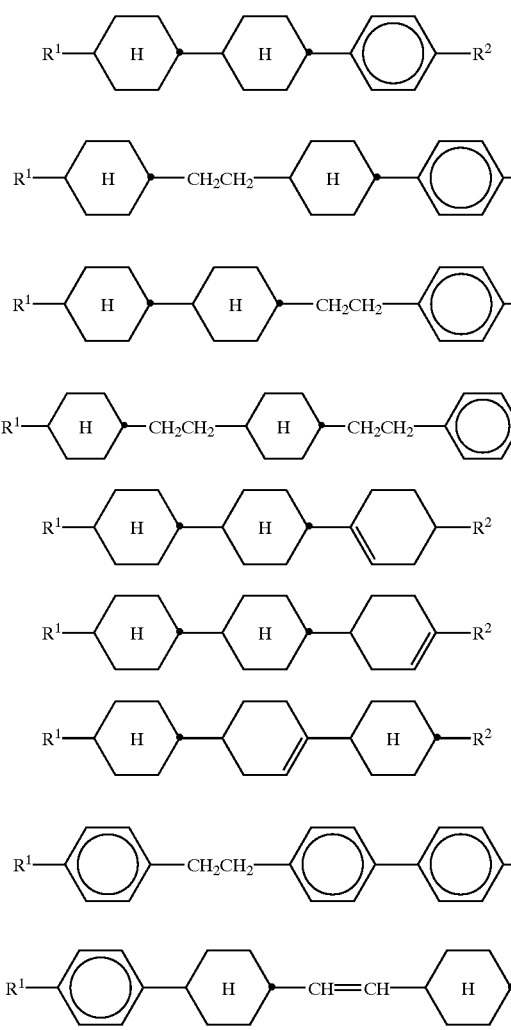

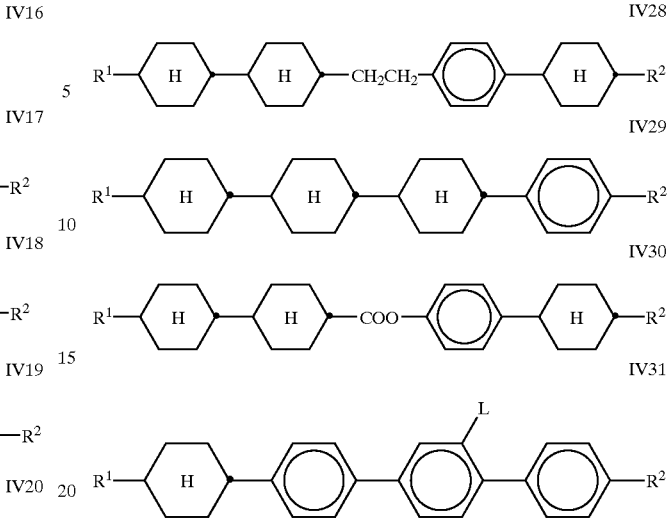

where $R^1$ and $R^2$ have the above-specified meaning and the 1,4-phenylene groups in IV10 to IV19, IV23 and IV24 can each, independently of one another, also be mono- or polysubstituted by fluorine.

Component B preferably comprises one or more compounds selected from the group consisting of the compounds of formulae IV25 to IV31:

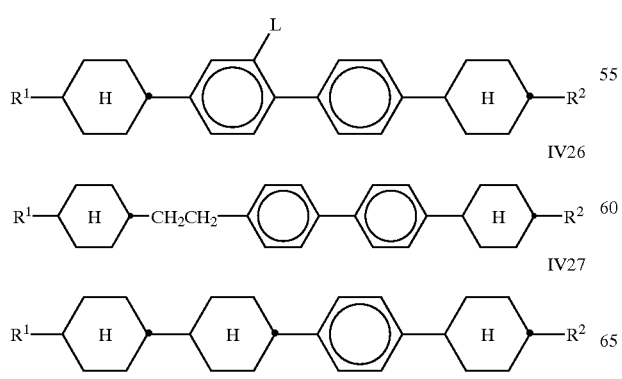

where $R^1$ and $R^2$ have the above-specified meaning and L is F or H. The 1,4-phenylene groups in the compounds IV25 to IV31 can each, independently of one another, also be mono- or polysubstituted by fluorine.

Particularly preferred are compounds of formulae IV25 to IV31, where $R^1$ is alkyl and $R^2$ is alkyl or alkoxy, particularly alkoxy, each having from 1 to 7 C atoms. Also preferred are compounds of formulae IV25 and IV31, where L is F.

$R^1$ and $R^2$ in the compounds of formulae IV1 to IV30 are particularly preferably straight-chain alkyl or alkoxy having from 1 to 12 C atoms.

Component B optionally comprises one or more compounds selected from the group consisting of the compounds of formulae VI and VII:

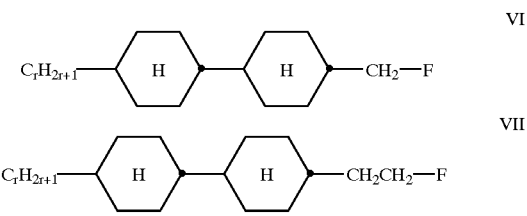

where $C_rH_{2r+1}$ is a straight-chain alkyl group and r is an integer from 1 to 9.

In a particularly preferred embodiment, the mixtures comprise one or more alkenyl compounds of formula V,

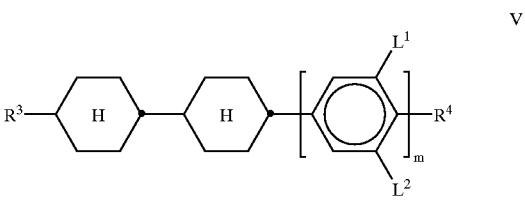

where
$R^3$ is an alkenyl group having from 2 to 7 C atoms,
$R^4$ has one of the meanings specified for $R^1$ or, if m is 1, may alternatively be Q—Y,
Q is —$CF_2$—, —$OCF_2$—, —CFH—, —OCFH— or a single bond, Y is F or Cl,
m is 0 or 1, and
$L^1$ and $L^2$ each, independently of one another, are H or F.
Formula V encompasses the following compounds

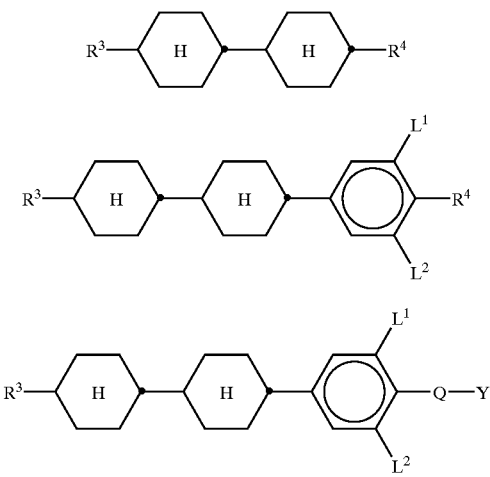

where $R^3$, $L^1$, $L^2$, Q and Y have the above-specified meanings, and $R^4$ has one of the meanings specified for $R^1$.

Particularly preferred are TN and STN displays according to the invention, which comprise at least one compound of formula V-1 and/or V-3, particularly preferably at least one compound of each of formulae V-1 and V-3.

In the formulae V-1, V-2 and V-3, $R^3$ particularly preferably is 1E-alkenyl or 3E-alkenyl having from 2 to 7 C atoms.

Preferred compounds of formula V-1 are those where $R^4$ is alkenyl having from 2 to 7 C atoms. Particularly preferred are compounds of the following formulae

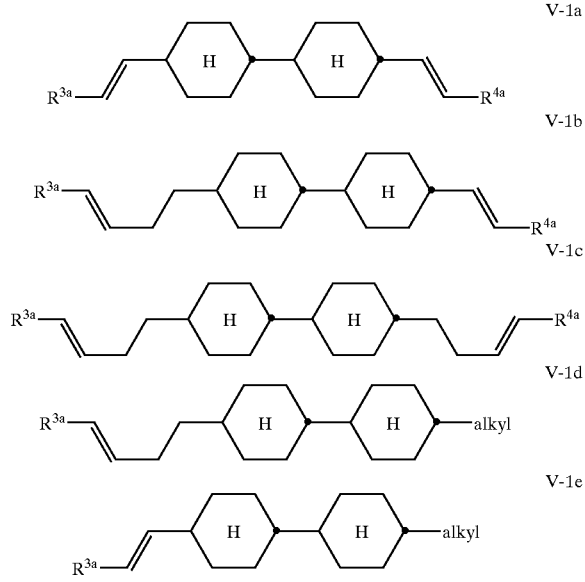

where $R^{3a}$ and $R^{4a}$ each, independently of one another, are H, $CH_3$, $C_2H_5$ or $n$-$C_3H_7$, and alkyl is an alkyl group having from 1 to 7 C atoms.

Particularly preferred are TN and STN displays according to the invention, in which the liquid crystal mixture comprises at least one compound of formulae V-1a and/or V-1c, in which $R^{3a}$ and $R^{4a}$ each have the same meaning, and displays in which the liquid crystal mixture comprises at least one compound of formula V-1e.

In a further preferred embodiment, the TN and STN displays comprise one or more compounds of formula V-2.

Particularly preferred compounds of formula V-2 are those where $L^1$ and $L^2$ are H, and those where $R^4$ is alkyl having from 1 to 8, in particular 1, 2 or 3 C atoms, and $R^3$ is 1E-alkenyl or 3E-alkenyl having from 2 to 7, particularly 2, 3 or 4 C atoms.

Most particularly preferred compounds of formula V2 are those of the following formulae

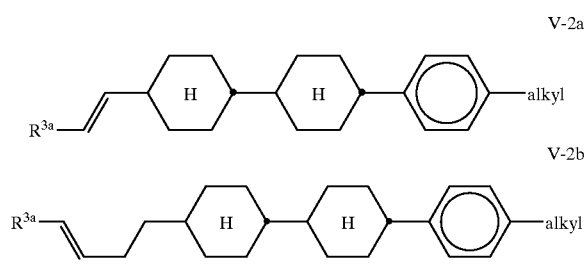

where $R^{3a}$, $R^{4a}$ and alkyl have the above-specified meaning, especially those where $R^{3a}$ is H.

Particularly preferred compounds of formula V-3 are those where $L^1$ and/or $L^2$ are F, and Q—Y is F or $OCF_3$. Also preferred are compounds of formula I-3, where $R^3$ is 1E-alkenyl or 3E-alkenyl having from 2 to 7, particularly 2, 3 or 4 C atoms.

The compounds of formulae V-1 and V-2 having a dielectric anisotropy of from −1.5 to +1.5 are to be classified with the above-defined component B. The polar compounds of formulae V-2 and V-3 having a dielectric anisotropy of more than +1.5 are to be classified with the above-defined component A.

The use of compounds of formula V in the liquid crystal mixtures according to the invention results in particularly low values of rotational viscosity and in TN and STN displays having high steepness and rapid switching times, particularly at low temperatures.

In a further preferred embodiment, the liquid crystal mixtures according to the invention comprise not only the components A, B, C and D, but also one or more compounds from the group of the compounds of formulae VIII and IX

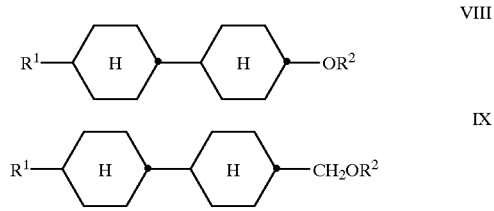

where $R^1$ and $R^2$ have the above-specified meanings.

Further preferred are liquid crystal mixtures comprising at least one component selected from the group consisting of the compounds of formulae X to XIV:

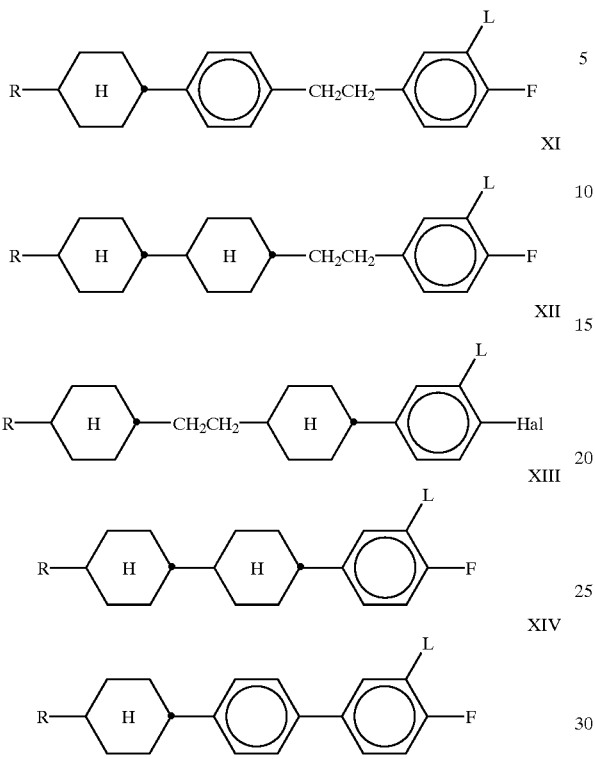

where Hal is F or Cl, and L is H or F, and R has the above-specified meaning, particularly where R is alkyl having from 1 to 12 C atoms.

The liquid-crystalline mixtures optionally comprise an optically active component D in such an amount that the ratio between layer thickness (spacing of the substrates) and natural pitch of the chiral nematic liquid crystal mixture is greater than 0.2. For this component, those skilled in the art have at their disposal a multiplicity of chiral dopants, some of which are commercially available, e.g. cholesteryl nonanoate, S-811 from Merck KGaA, Darmstadt, and CB15 (BDH, Poole, UK). The choice of dopants is not critical per se.

The proportion of compounds of component D is preferably 0 to 10%, in particular from 0 to 5%, particularly preferably from 0 to 3%.

In a particularly preferred embodiment, the mixtures according to the invention, in addition to the compounds of formula IB, comprise from about 2 to 65%, particularly from 5 to 35%, of liquid-crystalline tolane compounds. This allows smaller layer thicknesses to be employed, resulting in distinctly shorter switching times. The tolane compounds are preferably selected from group T consisting of the compounds of formulae T1 and T2:

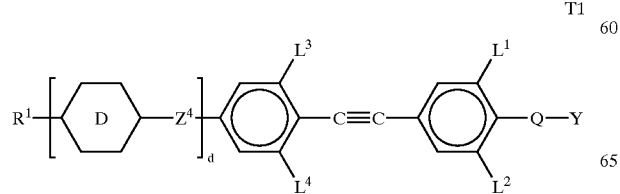

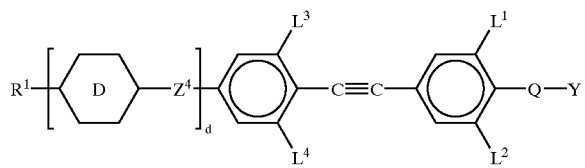

where

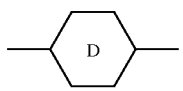

is

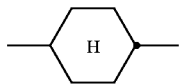

or

preferably

in formula T1 alternatively

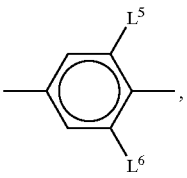

in formula T2 alternatively

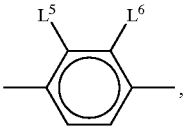

d is 0 or 1,
$L^1$ to $L^7$ each, independently of one another, are H or F,
Q is —$CF_2$—, —CHF—, —$OCF_2$—, —OCHF— or a single bond,
Y is F or Cl,
$Z^4$ is —CO—O—, —$CH_2CH_2$— or a single bond, and
$R^1$ and $R^2$ have the above-specified meanings.
Preferred compounds of formula T1 correspond to the subformulae T1a and T1b

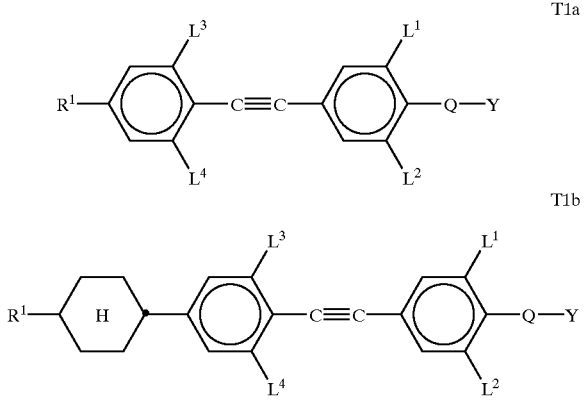

where $L^1$ to $L^4$ are H or F, and Q—Y is F, Cl or $OCF_3$, particularly F or $OCF_3$.

Preferred compounds of formula T2 correspond to the subformulae T2a to T2g

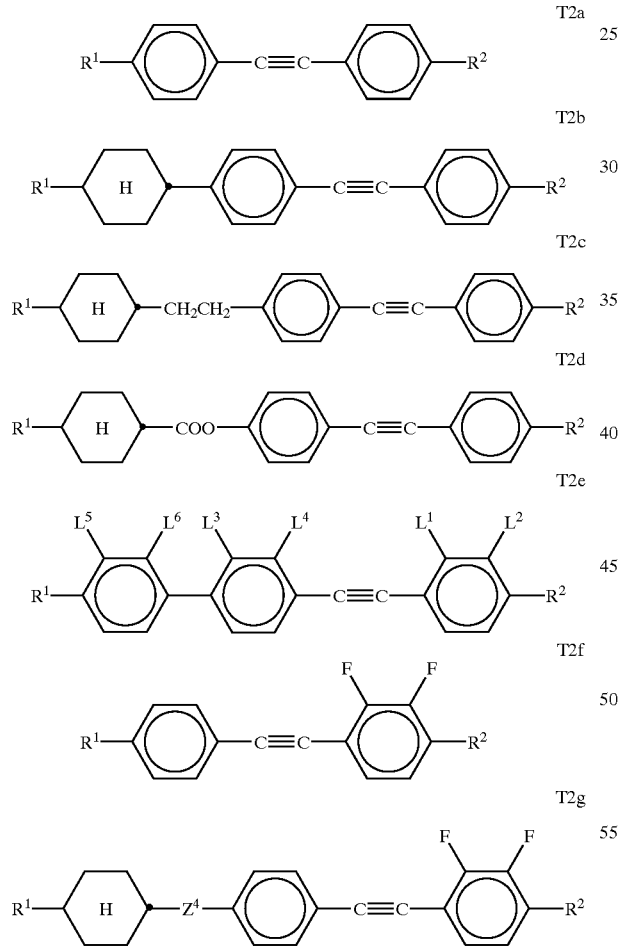

where $R^1$, $R^2$ and $Z^4$ have the above-specified meanings, and $L^1$ to $L^6$ are H or F.

Particularly preferred compounds of formula T2e are those where one, two or three of the radicals $L^1$ to $L^6$ are F and the others are H, $L^1$ and $L^2$ or $L^3$ and $L^4$ or $L^5$ and $L^6$ not simultaneously being F.

The proportion of the compounds from group T is preferably from 2 to 65%, particularly from 5 to 35%.

The mixtures according to the invention may optionally comprise up to 20% of one or more compounds having a dielectric anisotropy of <−2 (component C).

If the mixtures comprise compounds of component C, these are preferably one or more compounds having the structural element 2,3-difluoro-1,4-phenylene, e.g. compounds according to DE-A-38 07 801, 38 07 861, 38 07 863, 38 07 864 or 38 07 908. Particularly preferred are tolanes having said structural element according to international patent application PCT/DE 88/00133, particularly the abovementioned tolanes of formula T2 and their preferred subformulae.

Further known compounds of component C are, for example, derivatives of the 2,3-dicyanohydroquinones or cyclohexane derivatives having the structural element

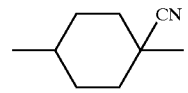

or

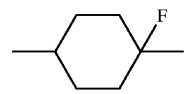

according to DE-A-32 31 707 and DE-A-34 07 013.

Preferably, the liquid crystal displays according to the invention do not comprise any compounds of component D.

The liquid crystal mixture according to the invention preferably comprises one or more compounds selected from group B1 consisting of compounds of formulae B1I to B1IV:

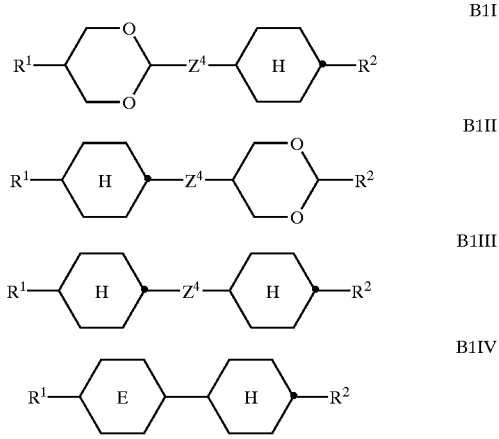

where $R^1$, $R^2$ and $Z^4$ have the above-specified meanings, and

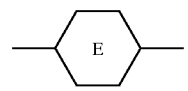

is

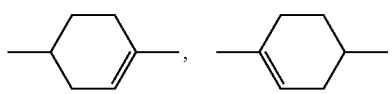

or

and/or at least one compound selected from group B2 consisting of compounds of formulae B2I to B2III:

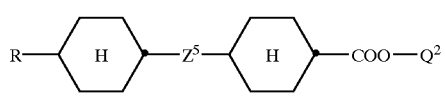

B2I

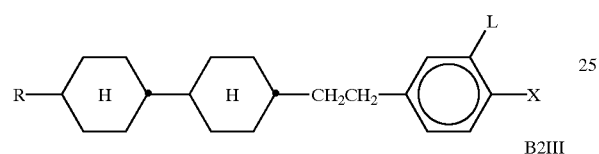

B2II

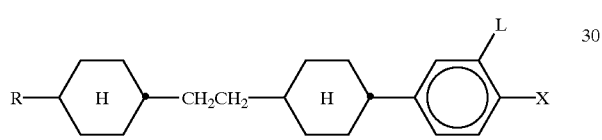

B2III where
R has the above-specified meaning,
$Z^5$ is —CH$_2$CH$_2$—, —CO—O— or a single bond,
$Q^2$ is

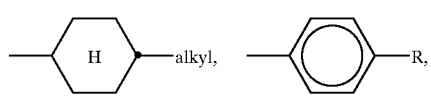

or

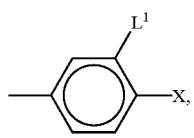

alkyl is an alkyl group having from 1 to 9 C atoms,
X is CN or F, and
L is H or F,
and/or at least one compound selected from group B3 consisting of compounds of formulae B3I to B3III:

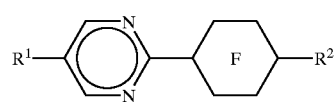
B3I

-continued

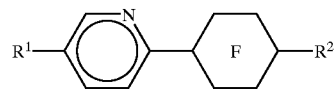
B3II

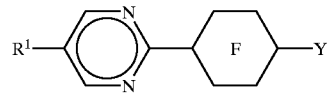
B3III where
$R^1$ and $R^2$ independently of one another have the above-specified meanings,
Y is F or Cl, and

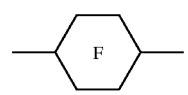

is

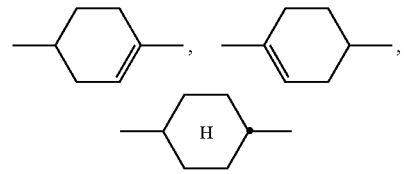

or

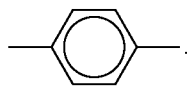

The proportion of the compounds from group B1 is preferably from 10 to 50%, particularly from 15 to 40%. Compounds of formulae B1III and B1IV are preferred.
Particularly preferred compounds of group B1 are those having the following component formulae,

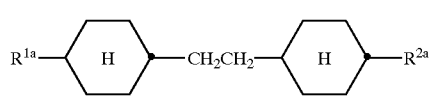
B1IIIa

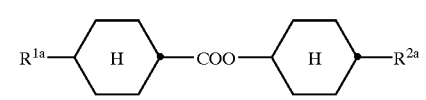
B1IIIb

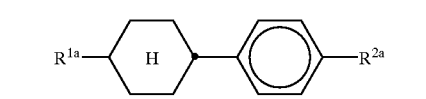
B1IVa where
$R^{1a}$ is CH$_3$—(CH$_2$)$_p$—, CH$_3$—(CH$_2$)$_p$—O—, CH$_3$—(CH$_2$)$_p$—O—CH$_2$—, trans-H—(CH$_2$)$_q$—CH=CH—(CH$_2$CH$_2$)$_s$—CH$_2$O— or trans-H—(CH$_2$)$_q$—CH=CH—(CH$_2$CH$_2$)$_s$—,
$R^{2a}$ is CH$_3$—(CH$_2$)$_p$—,
p is 1, 2, 3 or 4,
q is 0, 1, 2 or 3, and
s is 0 or 1.

The proportion of compounds of the above-specified component formulae B1IIIa and B1IIIb together with the compounds of formula IB1 is preferably from about 5 to 45%, particularly preferably from about 10% to 35%.

The proportion of compounds of component formula B1IVa or compounds of formula B1IV is preferably from about 5 to 40%, particularly preferably from about 10 to 35%.

In a particularly preferred embodiment, the mixtures simultaneously comprise compounds of formulae B1III and B1IV together with the compounds of formulae IB1 and IB2, the overall proportion for components of group B1 being maintained.

If compounds of formulae B1I and/or B1III are present, $R^1$ and $R^2$ each preferably are, independently of one another, n-alkyl having from 1 to 7 C atoms or (trans)-n-alkenyl having from 3 to 7 C atoms. Z is preferably a single bond.

Also preferred are mixtures according to the invention which comprise one or more compounds of formula B1IV, where

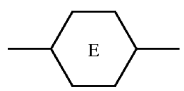

is

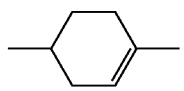

or

, and $R^1$ and $R^2$ have one of the above-specified preferred meanings and, in particular, preferably n-alkyl having from 1 to 7 C atoms.

In each instance, the overall proportion for components of group B1 is maintained.

The proportion of compounds of group B2 is preferably from about 5 to 45%, in particular from 5 to 20%. The proportion (preferred ranges) for B2I to B2III is as follows:

B2I: from about 5 to 30%, preferably from about 5 to 15%,

Sum of B2II and B2III: from about 5 to 25%, preferably from about 10 to 20%.

Preferred compounds of group B2 are listed below:

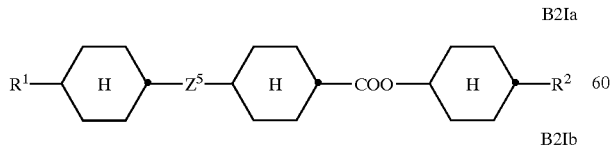

B2Ia

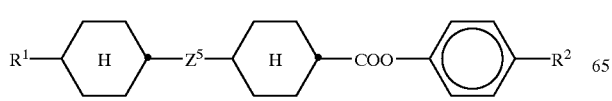

B2Ib

-continued

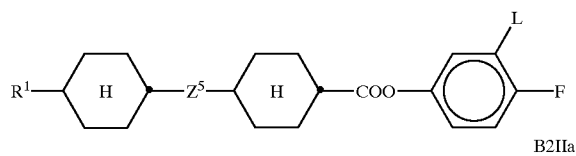

B2Ic

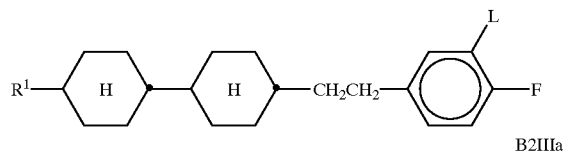

B2IIa

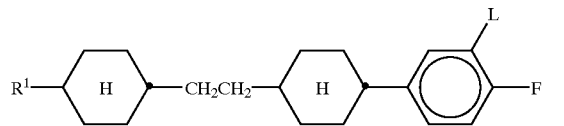

B2IIIa where $R^1$, $R^2$, L and $Z^5$ have the above-specified meanings.

$R^1$ in these compounds is preferably n-alkyl having from 1 to 7 C atoms or (trans)-n-alkenyl having from 3 to 7 C atoms, $Z^5$ is preferably a single bond, $R^2$ preferably has the preferred meaning specified hereinabove for R or is fluorine, L is preferably fluorine.

Preferably, the mixtures according to the invention comprise one or more compounds selected from the group consisting of B2Ic, B2IIa and B2IIIa in an overall proportion of from about 5 to 35%.

In a particularly preferred embodiment, the mixtures above the invention comprise not only B2Ic, B2IIa, B2IIIa (L=F), but also further terminally fluorinated compounds, for example selected from the group consisting of

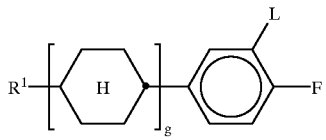

F1

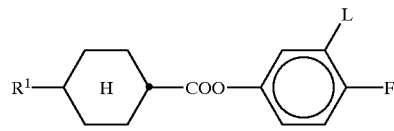

F2 and/or polar heterocyclic compounds selected from the group consisting of

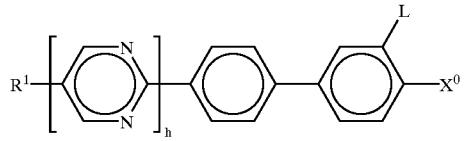

P1

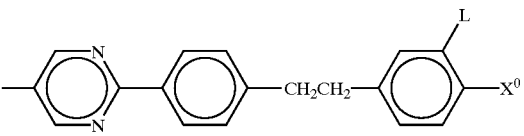

P2

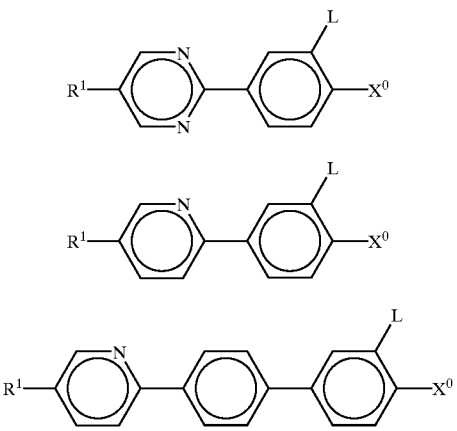

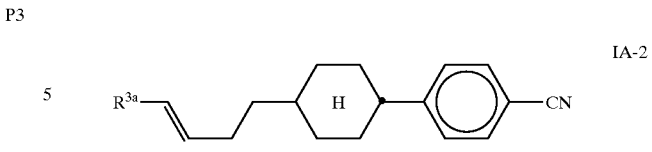

especially those where $R^{3a}$ is H or $CH_3$, most particularly preferably H, one or more compounds of the following formulae

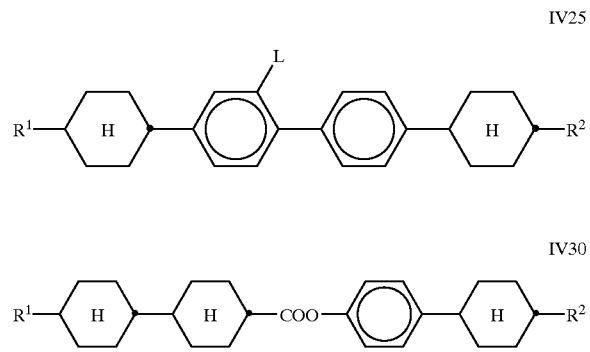

where $R^1$ is preferably n-alkyl having from 1 to 7 C atoms or (trans)-n-alkenyl having from 3 to 7 C atoms, g is 1 or 2, h is 0 or 1, $X^0$ is F, Cl, $CF_3$, —$OCF_3$ or —$OCHF_2$, and L is H or F.

The overall proportion of all the terminally fluorinated compounds is preferably from about 5 to 65%, in particular from about 15 to 40%.

The proportion of compounds from group B3 is preferably from about 5 to 30%, particularly preferably from about 10 to 20%. $R^1$ is preferably n-alkyl or n-alkoxy, either having from 1 to 9 C atoms.

Alternatively it is possible, however, for analogous compounds containing alkenyl or alkenyloxy groups to be used. Compounds of formula B3I are preferred.

The term "alkenyl" in the meaning of R, $R^1$, $R^2$, $R^3$ and $R^4$ encompasses straight-chain and branched alkenyl groups, having 2–12 carbon atoms in the case of R, $R^1$ and $R^2$, and having 2–7 carbon atoms in the case of $R^3$ and $R^4$, particularly the straight-chain groups. Particularly preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl, and $C_7$-6-alkenyl, particularly $C_2$–$C_7$-1E-alkenyl, $C_4$–$C_7$-3E-alkenyl and $C_5$–$C_7$-4-alkenyl.

Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

In a preferred embodiment, the liquid-crystalline media according to the invention comprise 3, 4, 5 or 6 compounds of formulae IA and IB; the proportion of these compounds as a rule is from 10 to 65 wt %, preferably from 15 to 50 wt %, based on the mixture as a whole.

In further preferred embodiments, the mixtures comprise one or more compounds of formula IB where L is F, one or more compounds of formula IA-1

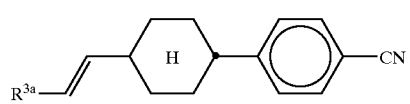

especially those where $R^{3a}$ is H or $CH_3$, most particularly preferably $CH_3$, where $R^1$, $R^2$ and L have the preferred meanings mentioned under compounds of component B. The proportion of these compounds in the liquid crystal mixtures is preferably from 0 to 45%, in particular from 5 to 30%, one or more, particularly 1, 2, 3 or 4 compounds, selected from the compounds of formulae IIIb, IIId, IIIf, IIIh, IIIi, IIIm, IIIs, IIIt and IIIu;

at least two compounds selected from the compounds of formulae IIb1, IIb2, IIc1 and IIc2. The proportion of these compounds in the liquid crystal mixtures is preferably from 0 to 60%, particularly from 10 to 45%;

at least one compound of formulae V-1, V-2 and/or V-3, particularly preferably at least one of each, in particular from 2 to 6, compounds selected from the following formulae:

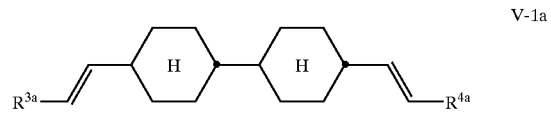

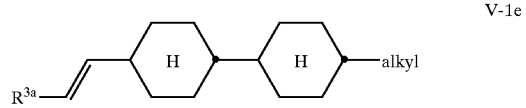

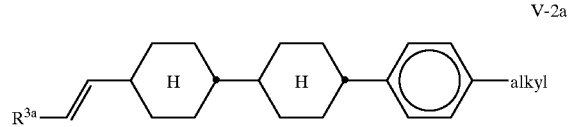

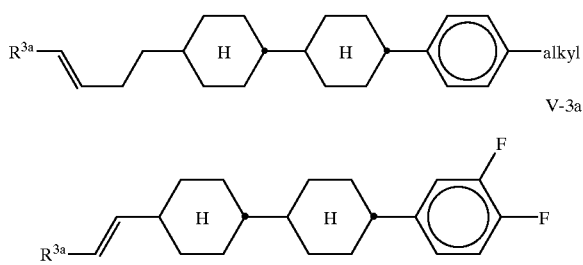

where $R^{3a}$ and $R^{4a}$ each, independently of one another, are H, $CH_3$, $C_2H_5$ or n-$C_3H_7$, $R^{3a}$ in particular is H, and alkyl is an alkyl group having from 1 to 7 C atoms, from 8 to 30%, particularly from 10 to 25%, of one or more compounds of formula IA, from 6 to 35%, particularly from 8 to 30%, of one or more compounds of formula IB.

Further particularly preferred embodiments relate to liquid crystal mixtures which comprise a total of from 2 to 6 compounds of formulae IA and IB, the proportion of these compounds in the overall mixture being from 15 to 65%, in particular from 20 to 55%, comprise at least 20%, in particular from 25 to 90%, particularly preferably from 32 to 80% of alkenyl compounds, particularly those of formulae IB and V, comprise more than 20% of compounds having a dielectric anisotropy $\Delta\epsilon \geq +12$, essentially consist of compounds of formulae IA, IB, V, IIc and/or IId and optionally additionally IV25 and IV30.

The mixtures according to the invention are distinguished, particularly when used in TN and STN displays having high layer thicknesses, by very low total switching times ($t_{tot} = t_{on} + t_{off}$). Low total switching times are an important criterion particularly for STN displays when used as laptop displays, to allow cursor movements to be shown in a trouble-free manner.

The liquid crystal mixtures used in the STN and TN cells according to the invention are dielectrically positive with $\Delta\epsilon \geq 1$. Particularly preferred are liquid crystal mixtures having $\Delta\epsilon \geq 3$, particularly those having $\Delta\epsilon \geq 5$.

The liquid crystal mixtures according to the invention exhibit useful values for the threshold voltage $V_{10/0/20}$ and for the rotational viscosity $\gamma_1$. If the optical path difference $d \cdot \Delta n$ has a predetermined value, the value of the layer thickness d is defined by the optical anisotropy $\Delta n$. Particularly for relatively high values of $d \cdot \Delta n$, the use of liquid crystal mixtures according to the invention having a relatively high value of the optical anisotropy is preferred, since a relatively small value of d can then be chosen, leading to more favourable values of the switching times. However, even those liquid crystal displays according to the invention which comprise liquid crystal mixtures according to the invention having smaller values of $\Delta n$ are characterized by advantageous values of the switching times.

The liquid crystal mixtures according to the invention are further characterized by advantageous values of the slope of the electro-optical characteristic curve and can be operated at high multiplex rates, especially at temperatures above 20° C. Moreover, the liquid crystal mixtures according to the invention exhibit high stability and favourable values of the electrical resistance and the threshold voltage frequency dependence. The liquid crystal displays according to the invention have a wide operating temperature range and good angular dependence of contrast.

The configuration of the liquid crystal display elements according to the invention, comprising polarizers, electrode baseplates and electrodes surface-treated in such a way that the preferential alignment (director) of the liquid crystal molecules adjoining each of these is usually twisted with respect to one another by an amount of from 160° to 720°, corresponds to the design customary for such display elements. In this context, the term "customary design" is to be interpreted broadly and also encompasses all alterations and modifications of the TN and STN cell, including matrix display elements in particular, and the display elements comprising additional magnets.

The surface tilt angle at the two substrates can be identical or different. Identical tilt angles are preferred. Preferred TN displays have pre-tilt angles between the longitudinal axis of the molecules at the surface of the substrates and the substrates of from 0° to 7°, preferably from 0.01° to 5°, in particular from 0.1 to 2°. In the STN displays the pre-tilt angle is from 1° to 30°, preferably from 1° to 12° and in particular from 3° to 10°.

The twist angle of the TN mixture in the cell amounts to between 22.5° and 170°, preferably between 45° and 130° and in particular to between 80° and 115°. In the display, the twist angle of the STN mixture, from alignment layer to alignment layer, amounts to between 100° and 600°, preferably to between 170° and 300° and in particular to between 180° and 270°.

The threshold voltage of the liquid crystal displays containing the nematic liquid crystal mixtures according to the instant application are preferably less than or equal to 1.85 V, more preferably less than or equal to 1.70 V and most preferably less than or equal to 1.65 V and in particular less than 1.40 V. These conditions apply for liquid crystal cells with a twist angle of 240° and a tilt angle of 4° or more.

Under these conditions the steepness ($V_{90}/V_{10}$) is preferably less than or equal 1.08, more preferably less than or equal to 1.07, more preferably less than or equal to 1.06 and most preferably less than or equal to 1.05.

The preparation of the liquid crystal mixtures usable according to the invention is performed in a manner customary per se. As a rule, the desired quantity of the components used in a smaller amount is dissolved in the components constituting the main constituent, expediently at elevated temperature. Alternatively it is possible to mix solutions of the components in an organic solvent, e.g. in acetone, chloroform or methanol and to remove the solvent again after thorough mixing, for example by distillation.

The dielectrics may further comprise additives known to those skilled in the art and described in the literature. For example, 0–15% of pleochroitic dyes can be added.

The entire disclosure of all applications, patents and publications, cited above or below, and of corresponding German Application No. 199 30 211.1, filed Jun. 30, 1999 is hereby incorporated by reference.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

In the present application and in the following examples, the structures of the liquid crystal compounds are given as acronyms, the transformation into chemical formulae being defined by the following tables A and B. All the radicals $C_nH_{2n+1}$ and $C_mH_{2m+1}$ are straight-chain alkyl radicals having n or m C atoms. The alkenyl radicals are in the trans configuration. Coding according to Table B is self-evident. Table A only lists the acronym for the parent structure. In individual cases, the parent structure acronym is followed, separated therefrom by a dash, by a code for the substituents $R^1$, $R^2$, $L^1$, $L^2$ and $L^3$:

| Code for $R^1$ $R^2$, $L^1, L^2, L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $OC_nH_{2n+1}$ | $C_mH_{2m+1}$ | H | H | H |
| nO.m | $C_nH_{2n+1}$ | $OC_mH_{2m+1}$ | H | H | H |
| n | $C_nH_{2n+1}$ | CN | H | H | H |
| nN.F | $C_nH_{2n+1}$ | CN | H | H | F |
| nN.F.F | $C_nH_{2n+1}$ | CN | H | F | F |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |
| nF.F | $C_nH_{2n+1}$ | F | H | H | F |
| nmF | $C_nH_{2n+1}$ | $C_mH_{2m+1}$ | F | H | H |
| nCF$_3$ | $C_nH_{2n+1}$ | CF$_3$ | H | H | H |
| nOCF$_3$ | $C_nH_{2n+1}$ | OCF$_3$ | H | H | H |
| n-Am | $C_nH_{2n+1}$ | —C≡C—$C_mH_{2m+1}$ | H | H | H |
| n-An | $C_nH_{2n+1}$ | —C≡C—CN | H | H | H |
| n-Vm | $C_nH_{2n+1}$ | —C=CH—$C_mH_{2m+1}$ | H | H | H |
| nV-Vm | $C_nH_{2n+1}$—CH=CH— | —C=CH—$C_mH_{2m+1}$ | H | H | H |
| Vn-m | CH$_2$=CH—$C_nH_{2n}$— | $C_mH_{2m+1}$ | H | H | H |
| nV-N | $C_nH_{2n+1}$—CH=CH— | CN | H | H | H |

The TN and STN displays preferably comprise liquid-crystalline mixtures which are composed of one or more compounds from Tables A and B.

TABLE A ($L^1$, $L^2$, $L^3$; H or F)

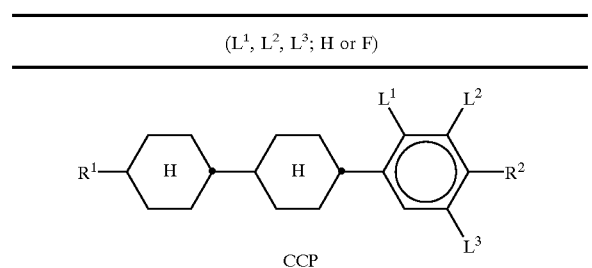

BCH

CBC

CCH

TABLE A-continued ($L^1$, $L^2$, $L^3$; H or F)

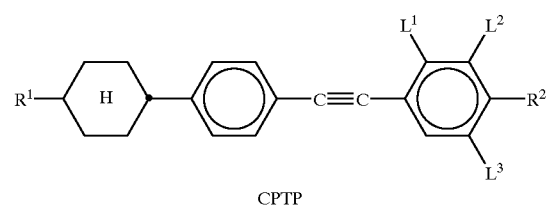

CCP

CPTP

PTP

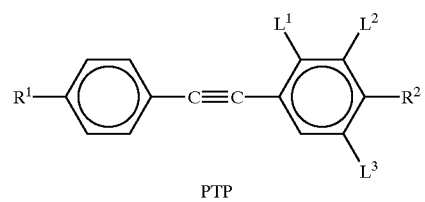

PCH

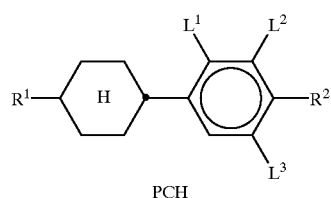

CCPC

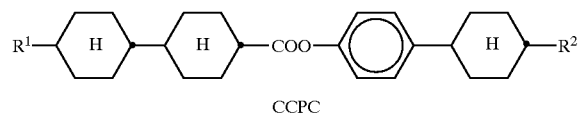

HP

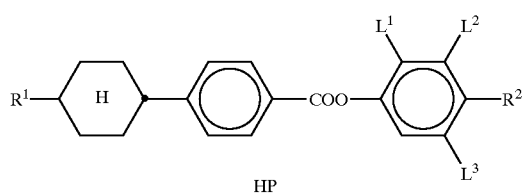

ME

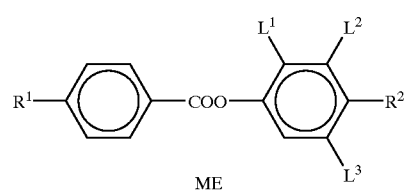

TABLE B

CCP-nV-m

CCG-V-F

CBC-nmF

CC-n-V

PPTUI-n-m

CC-nV-Vm

CP-nV-N

The following examples are intended to illustrate the invention without limiting it. The meaning of the symbols is as follows:

| | |
|---|---|
| S-N | phase transition temperature smectic-nematic, |
| N-I | phase transition temperature nematic-isotropic, |
| clp. | clearing point, |
| visc. | rotational viscosity (mPa * s), |
| $\Delta n$ | optical anisotropy (589 nm, 20° C.) |
| $t_{on}$ | time elapsed between switching on and reaching 90% of the maximum contrast |
| $t_{off}$ | time elapsed between switching off and reaching 10% of the maximum contrast |
| $V_{90}/V_{10}$ | steepness |
| $V_{op}$ | operating voltage |
| $t_{ave}$ | $\frac{t_{on}+t_{off}}{2}$ (mean switching time) |

Hereinabove and hereinafter, all temperatures are given in °C. Percentages are percent by weight. The values of the switching times and viscosities relate to 20° C., unless specified otherwise. The switching time, unless specified otherwise, is the mean value $t_{ave}$ of the switching-on and switching-off times.

Unless specified otherwise, the display is driven in multiplexed operation (multiplex ratio 1:16, bias 1:5).

Example 1

An STN mixture consisting of

| | | | |
|---|---|---|---|
| CP—1V—N | 10.50% | Clearing point: | 98.5° C. |
| PCH—3N.F.F | 2.00% | $\Delta n$: | 0.1414 |
| ME2N.F | 7.50% | Twist: | 240° |
| ME3N.F | 7.50% | $V_{10}$: | 1.66 V |
| ME4N.F | 6.50% | $V_{90}/V_{10}$: | 1.053 |
| CC-5-V | 5.50% | | |
| CC—1V—V1 | 8.25% | | |
| CCG-V—F | 14.00% | | |
| CCP—V-1 | 14.00% | | |
| CCP—V2-1 | 14.50% | | |
| PPTUI-3-2 | 8.25% | | |
| CCPC-33 | 1.50% | | |

Example 2

An STN mixture consisting of

| | |
|---|---|
| ME2N.F | 2.00% |
| ME3N.F | 2.50% |
| CP—1V—N | 17.00% |
| PYP-4 | 3.50% |
| CC-5-V | 12.00% |
| CCG-V—F | 18.00% |
| CCP—V-1 | 20.00% |
| CCP—V2-1 | 14.00% |
| PPTUI-3-2 | 11.00% |

Example 3

An STN mixture consisting of

| | |
|---|---|
| CP—1V—N | 15.00% |
| CP—V2—N | 15.00% |
| ME2N.F | 2.00% |
| CCP—V-1 | 15.00% |
| CCP—V2-1 | 2.50% |
| CCG-V—F | 19.00% |
| CC—1V—V1 | 8.00% |
| PPTUI-3-2 | 19.50% |
| CC-5-V | 4.00% |

Example 4

An STN mixture consisting of

| | |
|---|---|
| CP—1V—N | 14.00% |
| CP—V2—N | 14.00% |
| ME2N.F | 2.00% |
| CCP—V-1 | 13.00% |
| CCP—V2-1 | 2.00% |
| CCG-V—F | 19.00% |
| CC—1V—V1 | 8.00% |
| PPTUI-3-2 | 20.00% |
| CC-5-V | 8.00% |

Example 5

An STN mixture consisting of

| | | | |
|---|---|---|---|
| CP—1V—N | 15.00% | Clearing point: | 102.0° C. |
| CP—V2—N | 15.00% | Δn: | 0.1633 |
| ME2N.F | 2.00% | Twist: | 240° |
| CCP—V-1 | 15.00% | | |
| CCP—V2-1 | 2.00% | | |
| CCG-V—F | 19.00% | | |
| CC—1V—V1 | 8.00% | | |
| PPTUI-3-2 | 20.00% | | |
| CC-5-V | 4.00% | | |

Example 6

An STN mixture consisting of

| | | | |
|---|---|---|---|
| CP—1V—N | 23.00% | Clearing point: | 122.5° C. |
| PCH—3N.F.F | 15.00% | Δn: | 0.1958 |
| ME2N.F | 2.00% | Twist: | 240° |
| ME3N.F | 2.00% | $V_{10}$: | 1.84 V |
| CC-5-V | 3.00% | $V_{90}/V_{10}$: | 1.051 |
| CCP—V-1 | 8.00% | | |
| PPTUI-3-2 | 14.00% | | |
| PPTUI-3-4 | 14.00% | | |
| CCPC-33 | 3.00% | | |
| CCPC-34 | 4.00% | | |
| CBC-33F | 4.00% | | |
| CBC-53F | 4.00% | | |
| CBC-55F | 4.00% | | |

Example 7

An STN mixture consisting of

| | | | |
|---|---|---|---|
| CP—1V—N | 23.00% | CBC-33F | 4.00% |
| CP—V2—N | 6.00% | CBC-53F | 4.00% |
| PCH—3N.F.F | 11.00% | CBC-55F | 3.00% |
| ME2N.F | 2.00% | Clearing point: | 119.0° C. |
| ME3N.F | 2.00% | Δn: | 0.1948 |
| ME4N.F | 5.00% | Twist: | 240° |
| ME5N.F | 4.00% | $V_{10}$: | 1.59 V |
| PPTUI-3-2 | 12.00% | $V_{90}/V_{10}$: | 1.070 |
| PPTUI-3-4 | 12.00% | | |
| CCPC-33 | 5.00% | | |
| CCPC-34 | 4.00% | | |
| CCPC-35 | 4.00% | | |

Example 8

An STN mixture consisting of

| | | | |
|---|---|---|---|
| CP—1V—N | 25.00% | Clearing point: | 120.0° C. |
| CP—V2—N | 7.00% | Δn: | 0.1960 |
| PCH—3N.F.F | 12.00% | Twist: | 240° |
| ME2N.F | 4.00% | $V_{10}$: | 1.69 V |
| ME3N.F | 4.00% | $V_{90}/V_{10}$ | 1.029 |
| PPTUI-3-2 | 12.00% | | |
| PPTUI-3-4 | 12.00% | | |
| CCPC-33 | 4.00% | | |
| CCPC-34 | 4.00% | | |
| CCPC-35 | 4.00% | | |
| CBC-33F | 4.00% | | |
| CBC-53F | 4.00% | | |
| CBC-55F | 4.00% | | |

Example 9

An STN mixture consisting of

| | | | |
|---|---|---|---|
| CP—1V—N | 15.00% | Clearing point: | 102.5° C. |
| CP—V2—N | 15.00% | Δn: | 0.1647 |
| ME2N.F | 2.00% | Twist: | 240° |
| CCP—V-1 | 15.00% | | |
| CCP—V2-1 | 2.00% | | |
| CCG-V—F | 19.00% | | |
| CC-3-V1 | 8.00% | | |
| PPTUI-3-2 | 20.50% | | |
| CC-5-V | 3.50% | | |

Example 10

An STN mixture consisting of

| | | | |
|---|---|---|---|
| ME2N.F | 2.00% | Clearing point: | 98.0° C. |
| ME3N.F | 3.00% | Δn: | 0.1310 |
| ME4N.F | 5.00% | Twist: | 240° |
| CP—1V—N | 10.00% | $V_{10}$: | 2.10 V |
| CP—V2—N | 10.00% | $V_{90}/V_{10}$: | 1.039 |
| CC-5-V | 16.00% | | |
| CCG-V—F | 21.00% | | |
| CCP—V-1 | 11.00% | | |
| CCP—V2-1 | 9.00% | | |
| PPTUI-3-2 | 9.00% | | |
| CCPC-33 | 2.00% | | |
| CCPC-34 | 2.00% | | |

Example 11

An STN mixture consisting of

| | |
|---|---|
| ME2N.F | 2.00% |
| ME3N.F | 5.00% |
| ME4N.F | 7.00% |
| ME5N.F | 5.00% |
| CP—1V—N | 10.00% |
| CP—V2—N | 10.00% |
| CC-5-V | 7.00% |
| CCG-V—F | 21.00% |
| CCP—V-1 | 11.00% |
| CCP—V2-1 | 10.00% |
| PPTUI-3-2 | 5.00% |
| CCPC-33 | 4.00% |
| CCPC-34 | 3.00% |

Example 12

An STN mixture consisting of

| | | | |
|---|---|---|---|
| CP—1V—N | 14.00% | Clearing point: | 106.0° C. |
| CP—V2—N | 14.00% | Δn: | 0.1661 |
| ME2N.F | 3.00% | Twist: | 240° |
| ME3N.F | 3.00% | | |
| CCP—V-1 | 14.00% | | |
| CCP—V2-1 | 4.00% | | |
| CCG-V—F | 19.00% | | |
| CC-3-V1 | 8.00% | | |
| PPTUI-3-2 | 19.00% | | |
| CCPC-34 | 2.00% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A TN or STN liquid crystal display comprising
   two substrates which, together with an edging, form a cell,
   contained in the cell, a nematic liquid crystal mixture having positive dielectric anisotropy,
   electrode layers having alignment layers on the insides of the substrates,
   a pre-tilt angle between the longitudinal axis of the molecules at the surface of the substrates and the substrates of from 0 degrees to 30 degrees, and
   a twist angle of the liquid crystal mixture in the cell which, from alignment layer to alignment layer, amounts to between 22.5° and 600°,
   wherein the nematic liquid crystal mixture comprises
   a) 20–90 wt % of a liquid-crystalline component A, consisting of one or more compounds having a dielectric anisotropy of more than +1.5;
   b) 10–80 wt % of a liquid-crystalline component B, consisting of one or more compounds having a dielectric anisotropy of between −1.5 and +1.5;
   c) 0–20 wt % of a liquid-crystalline component C, consisting of one or more compounds having a dielectric anisotropy of less than −1.5 and
   d) an optically active component D in such an amount that the ratio between layer thickness (spacing of the substrates) and natural pitch of the chiral nematic liquid crystal mixture is from about 0.2 to 1.3,
   wherein component A of the mixture comprises at least one compound of formula IA,

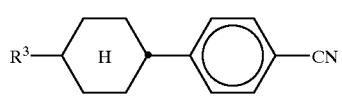

IA where
   $R^3$ is an alkenyl group having from 2 to 7 C atoms, and the mixture comprises at least one alkynyl-bonded compound of formula IB,

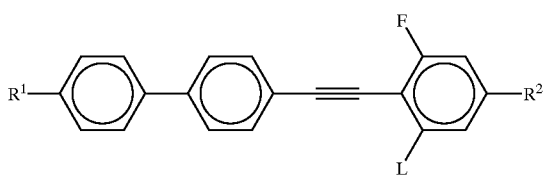

IB where
   $R^1$ and $R^2$ each, independently of one another, are an alkyl, alkoxy or alkenyl group having from 1 to 12 C atoms, with the additional option of 1 or 2 non-adjacent $CH_2$ groups being replaced by —O—, —CH=CH—, —CO—, —OCO— or —COO— in such a way that O atoms are not linked directly to one another, and
   L is H or F.

2. A liquid crystal display according to claim 1, wherein component A further comprises at least one of the following compounds

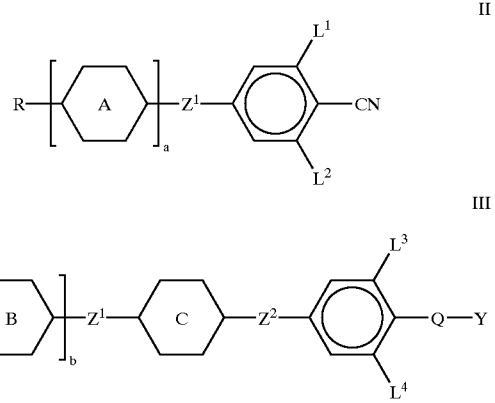

II

III where
   R is an alkyl, alkoxy or alkenyl group having from 1 to 12 C atoms, with the additional option of 1 or 2 non-adjacent $CH_2$ groups being replaced by —O—, —CH=CH—, —CO—, —OCO— or —COO— in such a way that O atoms are not linked directly to one another,

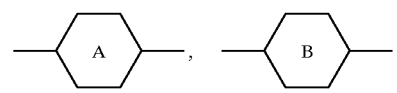

and

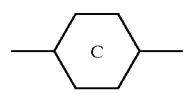

each, independently of one another, are

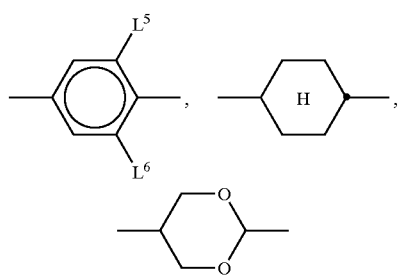

or

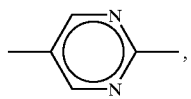

$L^1$ to $L^6$ each, independently of one another, are H or F,
   $Z^1$ is —COO—, —$CH_2CH_2$— or a single bond,
   $Z^2$ is —$CH_2CH_2$—, —COO—, —C≡C— or a single bond,
   Q is —$CF_2$—, —CHF—, —$OCF_2$—, —OCHF— or a single bond,
   Y is F or Cl,
   a is 1 or 2, and
   b is 0 or 1,
where, regarding formula II, the compounds according to formula IA from claim 1 are excluded.

3. A liquid crystal display according to claim 1, which comprises one or more alkenyl compounds of formula V,

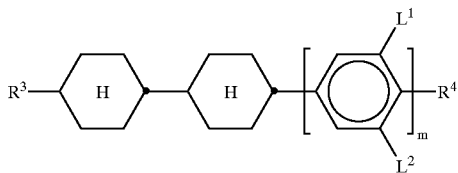

where
- $R^3$ is an alkenyl group having from 2 to 7 C atoms,
- $R^4$ has one of the meanings specified for $R^1$ or, if m is 1, may alternatively be Q—Y,
- Q is —$CF_2$—, —$OCF_2$—, —CFH—, —OCHF— or a single bond,
- Y is F or Cl,
- m is 0 or 1, and
- $L^1$ and $L^2$ each, independently of one another, are H or F.

4. A liquid crystal display according to claim 1, wherein component A further comprises one or more compounds of the following formulae

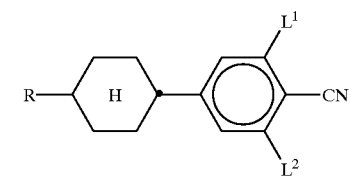

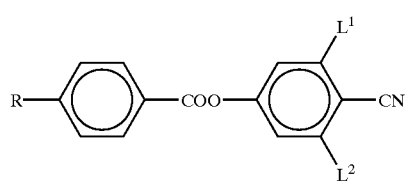

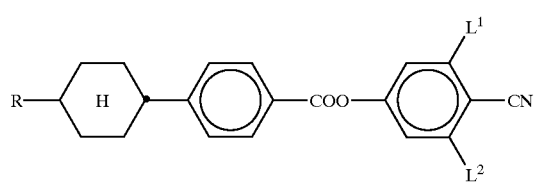

in which R is an alkyl, alkoxy or alkenyl group having from 1 to 12 C atoms, with the additional option of 1 or 2 non-adjacent $CH_2$ groups being replaced by —O—, —CH=CH—, —CO—, —OCO— or —COO— in such a way that O atoms are not linked directly to one another, and $L^1$ and $L^2$ each, independently of one another, are H or F; provided that for compounds of formula IIb, where $L^1$ and $L^2$ are H, R is an alkyl or alkoxy group.

5. A liquid crystal display according to claim 1, wherein the nematic liquid crystal mixture comprises one or more compounds of the following formulae

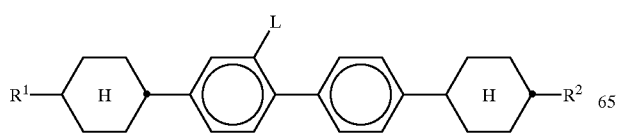

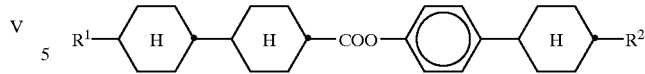

where $R^1$ and $R^2$ have the meaning specified in formula IB and L is H or F.

6. A liquid crystal display according to claim 1, which comprises from 25 to 90% of alkenyl compounds.

7. A liquid crystal display according to claim 1, which comprises from 8 to 30% of one or more compounds of formula IA.

8. A liquid crystal display according to claim 1, which comprises from 10 to 25% of one or more compounds of formula IA.

9. A liquid crystal display according to claim 1, which comprises from 6 to 35% of one or more compounds of formula IB.

10. A liquid crystal display according to claim 1, which comprises from 8 to 30% of one or more compounds of formula IB.

11. A liquid crystal display according to claim 7, which comprises from 6 to 35% of one or more compounds of formula IB.

12. A liquid crystal display according to claim 1, which comprises more than 20% of compounds having a dielectric anisotropy, $\Delta\epsilon \geq +12$.

13. A nematic liquid crystal mixture comprising
   a) 20–90 wt % of a liquid-crystalline component A, consisting of one or more compounds having a dielectric anisotropy of more than +1.5;
   b) 10–80 wt % of a liquid-crystalline component B, consisting of one or more compounds having a dielectric anisotropy of between −1.5 and +1.5;
   c) 0–20 wt % of a liquid-crystalline component C, consisting of one or more compounds having a dielectric anisotropy of less than −1.5 and
   d) an optically active component D in such an amount that the ratio between layer thickness (spacing of the substrates) and natural pitch of the chiral nematic liquid crystal mixture is from about 0.2 to 1.3,
wherein component A of the mixture comprises at least one compound of formula IA,

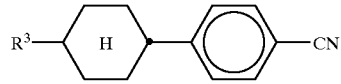

where
$R^3$ is an alkenyl group having from 2 to 7 C atoms, and the mixture comprises at least one alkynyl-bonded compound of formula IB,

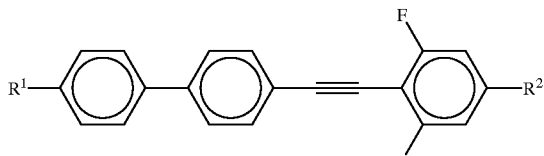

where
$R^1$ and $R^2$ each, independently of one another, are an alkyl, alkoxy or alkenyl group having from 1 to 12 C atoms, with the additional option of 1 or 2 non-adjacent $CH_2$ groups being replaced by —O—, —CH=CH—, —CO—, —OCO— or —COO— in such a way that O atoms are not linked directly to one another, and
L is H or F.

* * * * *